United States Patent [19]

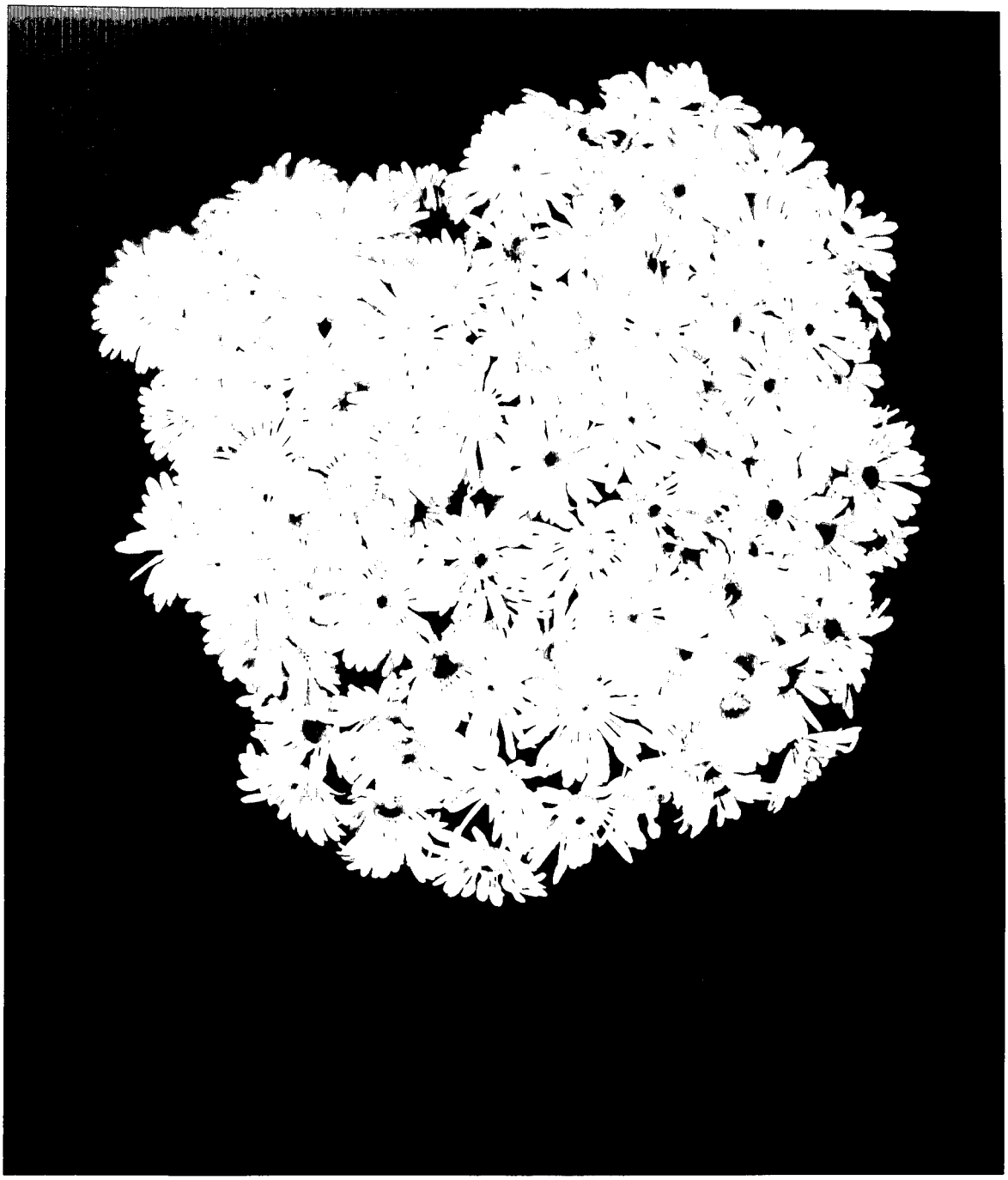

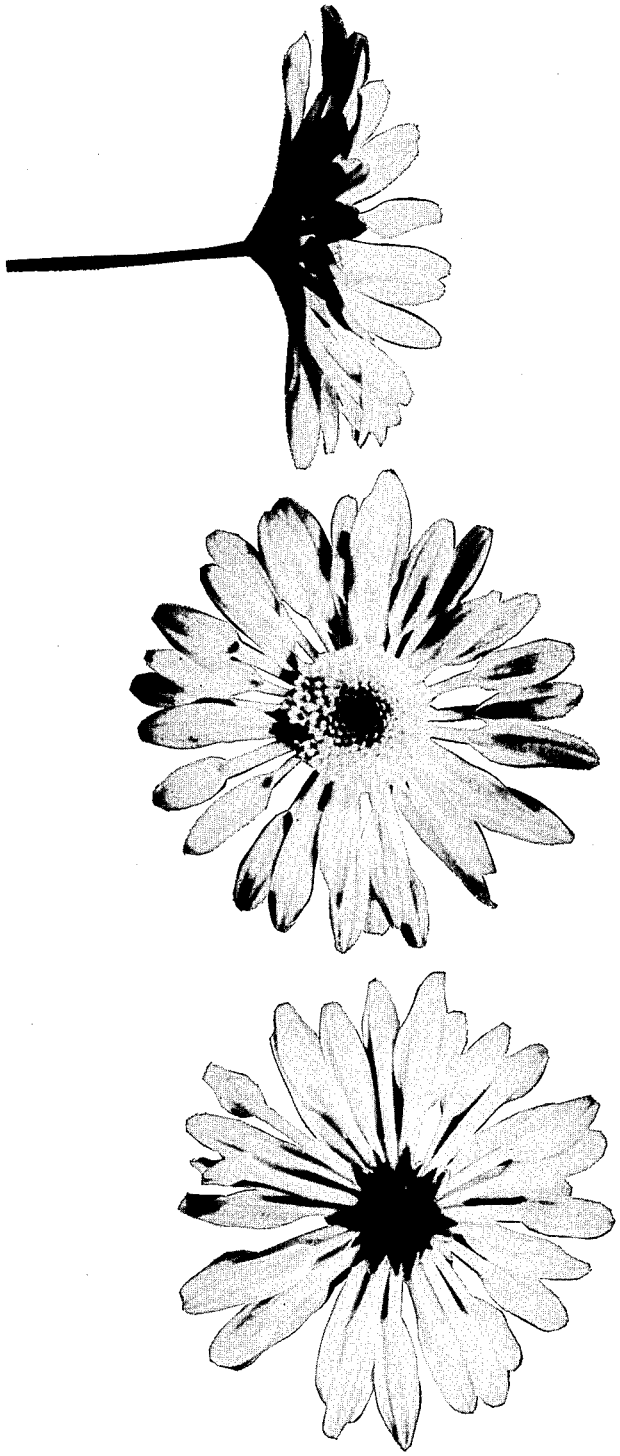

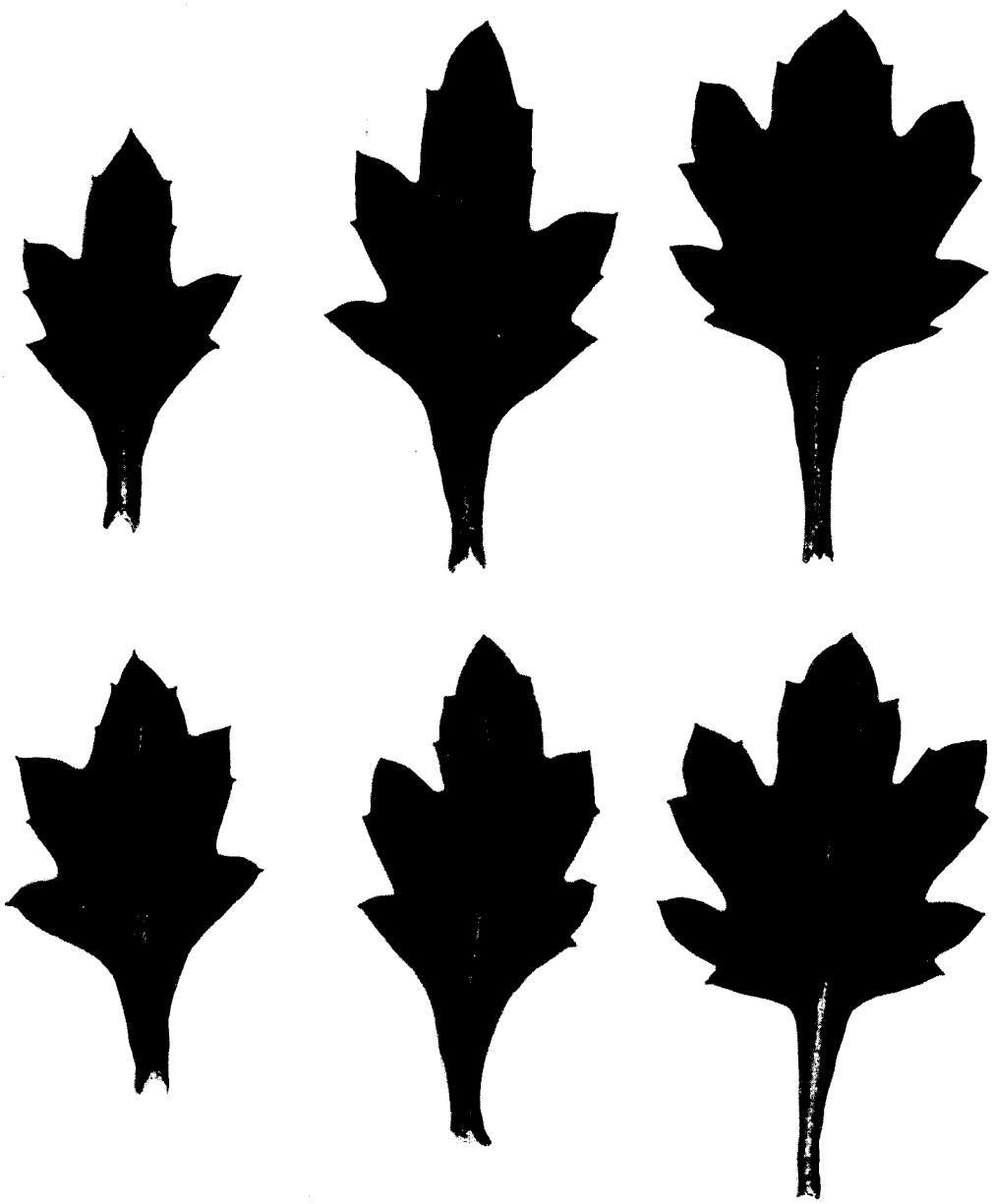

Duffett

[11] Patent Number: Plant 5,566

[45] Date of Patent: Oct. 1, 1985

[54] CHRYSANTHEMUM PLANT NAMED JOY

[75] Inventor: William E. Duffett, Salinas, Calif.

[73] Assignee: Yoder Brothers, Inc., Barberton, Ohio

[21] Appl. No.: 562,288

[22] Filed: Dec. 16, 1983

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of *Chrysanthemum morifolium,* Ramat., plant named Joy and particularly characterized as to uniqueness by the combined characteristics of flat and spooned capitulum form; anemone capitulum type; white ray floret color; diameter across face of capitulum ranging from 5 to 7 cm. at maturity; uniform 8 to 9 week flowering response; medium plant height; spreading, branching pattern; and uniform, 11 hour short day response to 24° C. night and 38° C. day temperatures under high light conditions.

3 Drawing Figures

The present invention comprises a new and distinct cultivar of *Chrysanthemum morifolium,* Ramat., named Joy.

Joy is a product of a planned breeding program which had the objective of creating new chrysanthemum cultivars for pinched, spray pot mum programs having anemone capitulum type, white floret color, eight week flowering response and the ability to produce commercially acceptable quality in year round programs. Such traits in combination were not present or required improvement in previously available commercial cultivars.

Joy was originated from a cross made by William E. Duffett in a controlled breeding program in Salinas, Calif. in 1978. The female parent was Songster, disclosed in U.S. Plant Pat. No. 5,028, originated by the present inventor from a hybridization of Quills, disclosed in U.S. Plant Pat. No. 4,401, and an unnamed seedling. The male parent to Joy was Echo, disclosed in U.S. Plant Pat. No. 4,973, originated from a cross between two unnamed seedlings.

Joy was discovered and selected as one flowering plant within the progeny of the stated cross by William E. Duffett on Nov. 21, 1980 in a controlled environment in Salinas, Calif.

The first act of asexual reproduction of Joy was accomplished when vegetative cuttings were taken from the initial selection in April 1981 in a controlled environment in Salinas, Calif. by a technician working under formulations established and supervised by William E. Duffett. Horticultural examination of selected units initiated October 1981 has demonstrated that the combination of characteristics as herein disclosed for Joy are firmly fixed and are retained through successive generations of asexual reproduction.

Joy has not been observed under all possible environmental conditions. The phenotype may vary significantly with variations in environment such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Joy, which in combination distinguish this chrysanthemum as a new and distinct cultivar:

(1) Flat and spooned capitulum form.

(2) Anemone capitulum type.

(3) White ray floret color.

(4) Diameter across face of capitulum ranging from 5 to 7 cm. at maturity.

(5) Uniform 8 to 9 week photoperiodic flowering response to short days.

(6) Medium plant height (requiring 2 long day weeks prior to pinch and short days and 1 to 2 applications of 2500 ppm B9 SP, the first at 14, the second at 21 days after the beginning of short days to attain a flowered plant height of 25 to 35 cm. in 6" pots).

(7) Spreading branching pattern.

(8) Uniform 11 hour short day response to 24° C. night and 38° C. day temperatures under high light conditions.

The accompanying photographic drawings depict typical leaf and inflorescence characteristics of Joy. Sheet 1 is a color photograph of a plant of Joy grown as a pinched, spray pot mum, with colors being as accurate as possible with renditions of this type. Sheet 2 is a black and white photograph of three views of the inflorescence of Joy. Sheet 3 shows the leaves of Joy in three stages of growth (mature, intermediate, immature).

Of the many commercial cultivars known to the present inventor, the most similar in comparison to Joy is Echo, disclosed in U.S. Plant Pat. No. 4,973. Reference is made to attached Chart A which compares certain characteristics of Joy to those same characteristics of Echo.

Joy differs from Echo by developing a whiter ray floret color, a higher percent of ray florets with shorter length of tubes, shorter response time and a more spreading, branching pattern. The capitulum type and diameter and plant height are similar.

In the following description, color references are made to The Royal Horticultural Society Colour Chart. The color values were determined between 2:00 and 2:30 P.M. on Sept. 7, 1983 under 150 foot-candle light intensity at Salinas, Calif.

Classification:

*Botanical.—Chrysanthemum morifolium,* Ramat., cv Joy.

*Commercial.*—Anemone Spray Pot Mum.

I. Inflorescence:

A. *Capitulum.*—Form: Flat and spooned. Type: Anemone. Diameter Across Face: 5 to 7 cm.

B. *Corolla of ray florets.*—Color (General Tonality From A Distance of Three Meters): White with yellow-green cushion. Color (abaxial): 155D. Color (adaxial): 155D. Shape: Base and lower section generally tubular. Upper section flat with rounded tip. Oar shaped. Day-night temperatures of 38° C. to 24° C. results in the development of a higher percentage of flat ray florets or reduction of length of tube as compared with 27° C. to 16° C. when a higher percent of spoon formed ray florets develop with longer tubes.

C. *Corolla of disc florets.*—Color (mature): 12A–B oxidizing to 155B. Color (immature): 144B to 144C.

D. *Reproductive organs.*—Androecium: Present disc florets only; scant pollen. Gynoecium: Present both ray and disc florets.

II. Plant:

A. *General appearance.*—Height: Medium. Branching Pattern: Spreading

B. *Foliage.*—Color (abaxial): 137A–B. Color (adaxial): 138A–B. Shape: Shallow lobed. Deeply serrated.

CHART A

COMPARISON OF JOY AND ECHO

| CULTIVAR | RAY FLORET COLOR | CAPITULUM FORM AND TYPE | BRANCHING PATTERN |
|---|---|---|---|
| JOY | WHITE | FLAT SPOON ANEMONE | SPREADING |
| ECHO | IVORY WHITE | FLAT SPOON ANEMONE | UPRIGHT |

| CULTIVAR | DIAMETER ACROSS FACE OF CAPITULUM | PLANT HEIGHT | FLOWERING RESPONSE PERIOD |
|---|---|---|---|
| JOY | 5 to 7 cm. | MEDIUM 25 to 30 cm. | 8–9 WEEKS |
| ECHO | 7 to 7.5 cm. | MEDIUM 25 to 35 cm. | 9 WEEK |

COMPARISONS MADE OF PLANTS GROWN AS PINCHED SPRAY POT MUMS IN SALINAS, CALIFORNIA AND LEAMINGTON, ONTARIO, CANADA

I claim:

1. A new and distinct cultivar of *Chrysanthemum morifolium,* Ramat., plant named Joy, as described and illustrated, and particularly characterized as to uniqueness by the combined characteristics of flat and spooned capitulum form; anemone capitulum type; white ray floret color; diameter across face of capitulum ranging from 5 to 7 cm. at maturity; uniform 8 to 9 week flowering response; medium plant height; spreading, branching pattern; and uniform, 11 hour short day response to 24° C. night and 38° C. day temperatures under high light conditions.

* * * * *